United States Patent [19]
O'Neil et al.

[11] Patent Number: 6,044,843
[45] Date of Patent: Apr. 4, 2000

[54] MOISTURE RESISTANT AIRWAY ADAPTER FOR MONITORING CONSTITUENT GASES

[75] Inventors: Michael P. O'Neil, Sunnyvale; Ross Flewelling, Oakland; John A. Culver, deceased, late of San Francisco, all of Calif., by Kristine J. Culver-Barrett, executor

[73] Assignee: Nellcor Puritan Bennett Incorporated, Pleasanton, Calif.

[21] Appl. No.: 08/863,637

[22] Filed: May 28, 1997

[51] Int. Cl.[7] .................................................. A61M 16/00
[52] U.S. Cl. ............................ 128/204.23; 128/207.14; 600/529
[58] Field of Search ..................... 128/204.23, 207.14, 128/205.23, 200.21, 200.24, 204.16, 203.12; 600/532, 529, 533

[56] References Cited

U.S. PATENT DOCUMENTS

| | | | |
|---|---|---|---|
| 5,789,660 | 8/1998 | Kofoed et al. | 128/219 |
| 5,807,636 | 9/1998 | Sheu et al. | 428/403 |

*Primary Examiner*—John G. Weiss
*Assistant Examiner*—Charles W. Anderson
*Attorney, Agent, or Firm*—Townsend and Townsend and Crew LLP

[57] ABSTRACT

An airway adapter comprising a tubular portion having opposing windows in a predetermined spaced configuration. The windows have at least one surface which interacts with moisture condensed thereon from respiratory gases so as to reduce the interference of such condensation with the measurement of constituent gases by a gas analyzer. The surface of the windows can be hydrophobic, hydrophilic, or a combination thereof.

24 Claims, 5 Drawing Sheets

MOISTURE RESISTANT AIRWAY ADAPTER FOR MONITORING CONSTITUENT GASES

BACKGROUND OF THE INVENTION

The present invention relates generally to airway adapters used with gas analyzers for monitoring constituent respiratory gases in a patient. The present invention relates particularly to an airway adapter with a surface confronting the airway which interacts with water in the patient's breath so as to reduce the impact of water on the monitoring of the constituent gases.

It has long been recognized in the anesthetic and other health care related arts that monitoring respiration is a very reliable method of determining the condition of a patient and, moreover, is one which provides an instant indication of adverse conditions as compared with other life signs which take longer periods to depart from normal values. Such an immediate indication is of great interest in connection with patients undergoing surgery or who are in other life-threatening situations, and in connection with monitoring infants who are subject to cessation of breathing (apnea) for no apparent cause.

Respiratory gas analyzers function by passing electromagnetic radiation (typically light) of a specific wavelength (typically infrared) through the respiratory gas and measuring the absorption for a component being monitored (such as $CO_2$). One method of monitoring breathing which has been used extensively involves monitoring the difference in carbon dioxide ($CO_2$) content between an individual's inspired and expired gas streams. It is impossible to breathe without the carbon dioxide content of the expired gas stream varying from that of the inspired gas stream by at least about 2%.

Capnography, the measurement of carbon dioxide levels in the airway, is one particular monitoring technology that aids clinicians in critical patient management decisions. Capnography assists clinicians in patient management decisions by providing the means to assess a large number of problems related to ventilation, cardiopulmonary functions and metabolism. Capnography can help clinicians monitor the integrity of gas delivery systems and mechanical ventilators as well. It can provide early warning of events which may indicate an obstruction of the patient's airway tube or disconnection of the ventilatory circuit, the onset of pulmonary disease or changes in physiologic status. In addition, waveforms displayed on a monitor corresponding to carbon dioxide concentrations may be used by clinicians to assess emphysema, asthma, chronic bronchitis, pneumonia and cardiac arrest.

Most capnometers are comprised of an airway adapter (sometimes referred to as a cuvette), an emitter, a detector, and a processor. The constituent gas flows through the airway adapter and between the emitter and detector, which are placed behind windows on either side of the airway adapter. Measurement is made directly through the windows. The detector receives the energy that is transmitted by the emitter that is not absorbed by the constituent gas, and the processor processes the signal from the detector. For example, emitted infrared light of a selected wavelength band is attenuated in correspondence to the quantity of carbon dioxide in the respiratory gas.

U.S. Pat. No. 4,648,396 (Raemer) discloses a respiration detector which features an infrared source and detector pair disposed on opposite sides of a cuvette through which the gas stream is inhaled and exhaled by a patient. U.S. Pat. No. 5,067,492 (Yelderman et al.) discloses a disposable endotracheal airway adapter that connects in series with a respirator or anesthesia breathing circuit and allows the passage of infrared radiation through the gases for measuring the constituent concentration of respiratory gases.

Conventional capnometers typically have problems associated with moisture buildup, calibration and warm-up time, which problems tend to limit their widespread acceptance. Respiratory gas contains substantial amounts of water vapor which condenses on the inner sides of the airway adapter and on the windows through which the light is passed for measuring a gas component. The gas analysis is impeded by this presence of saturated water vapor. In the closed environment of a patient ventilator, water continuously condenses on all surfaces of the airway adapter including the windows. Liquid water present on the airway adapter windows strongly absorbs infrared light at the wavelengths used to measure carbon dioxide, anesthetic agents and other gases, therefore making the measurement of carbon dioxide and other agents less precise and in some cases unreliable. The presence of individual liquid water droplets on the windows further contributes to such problems due to reflection and diffraction of the light used for measurement.

A conventional method of preventing condensation on airway adapter windows has been to heat the windows. U.S. Pat. No. 5,092,342 (Hattendorff et al.) discloses a sensor arrangement including a housing containing a transmitter, a receiver, and a heatable holder for a measuring cuvette. U.S. Pat. No. 5,146,092 (Apperson et al.) discloses an airway adapter with a heater provided to heat the casing of the airway adapter associated with a transducer to a temperature high enough to keep condensation from forming on the windows.

Heating the cuvette has a number of disadvantages. First, heating requires significant amounts of power, which is particularly limited in battery operated systems. Second, additional power and sensing lines increase the cost and weight of the system. Third, the mechanical design becomes complex as heat transfer issues are encountered. Lastly, warm-up time can delay the use of the sensor in emergency applications.

There is a continuing and long-felt need to provide a cost-effective way to prevent the condensation of water vapor on the inside of the windows in an airway adapter from interfering with the accuracy and reliability of measuring component respiratory gases.

SUMMARY OF THE INVENTION

The present invention provides an airway adapter with a window having a surface confronting the airway that controls the condensation formed on the window in the airway adapter. According to one embodiment, the surface of the window is sufficiently hydrophilic to cause the condensation on the window to be drawn out to form a layer of moisture so thin that it causes little interference with the gas analyzer measurements conducted through the windows. Alternatively, the surface of the window is sufficiently hydrophobic to cause the condensation to form in beads on the window so that the areas between the beads are sufficiently free from condensation so that gas analyzer measurements can be made through those areas. According to a further embodiment of this invention, the surface of the window can be both hydrophilic and hydrophobic to provide the advantages set forth herein.

In accordance with one embodiment of the present invention, there is provided an airway adapter for use with a respiratory gas analyzer comprising a tubular portion having a window positioned whereby respiratory gases passing through the airway adapter flow past the window and being adapted to receive an emitter and a receiver for measuring through the window energy absorbance of a constituent gas in the respiratory gases, the window comprises at least one surface which interacts with moisture in the respiratory gases so as to reduce the interference of moisture with the measurement of the constituent gases by the gas analyzer. The surface of the windows can be hydrophobic, hydrophilic, or a combination thereof.

In another embodiment of the present invention, there is provided an airway adapter for use with a respiratory gas analyzer having a tubular portion having a film window positioned in a seat having a seating surface and a receiving surface. A securing member is pressed into the seat toward the seating surface to hold the film window taut so as to provide uniform optical transmission for measuring the optical absorbance of the constituent gas.

BRIEF DESCRIPTION OF THE DRAWINGS

Many objects and advantages of the present invention will be apparent to those of ordinary skill in the art when this specification is read in conjunction with the attached drawings. The invention will now be described with reference to the accompanying drawings wherein like reference numerals are applied to like elements and wherein.

DESCRIPTION OF THE PREFERRED EMBODIMENT

In one embodiment of the present invention (FIG. 1), there is provided an airway adapter 4 comprising a cuvette 2 which is used to prevent the patient respiratory gases being monitored from coming in contact with a respiratory gas analyzer sensor 3 which connects to gas analyzer 1. The gases being monitored can be carbon dioxide, oxygen, ethanol, metabolic trace gases such as acetone or anesthetic gases such as isoflurane, halothane, desflurane, sevoflurane and enflurane. The cuvette or conduit 2 is designed to connect in series with tubing used to connect a patient to a mechanical ventilator or anesthesia breathing circuit. The cuvette or conduit is not limited to being transparent. The airway adapter 4 is preferably very light weight so that it does not interfere with the breathing tube which is usually inserted into a patient's trachea. In addition to being a gas conduit, the cuvette or conduit 2 of the present invention provides an optical path through which the gas sensor 3 can pass electromagnetic radiation onto a sample of respiratory gas(es) for analysis.

The airway adapter 4 can be sterilized for re-use or disposed of after one use. Such single patient use saves sterilization expenses and eliminates cross-contamination. This is especially useful with highly contagious diseases such as tuberculosis, but is also a benefit in routine cases where an unknown disease may be carried but not active. Also, since the airway adapter 4 of the present invention is relatively small and light weight, it may be placed close to the patient's mouth so as to allow quantitative readings for purposes of determining the concentrations of the constituents in the expired gas.

Figure 1:
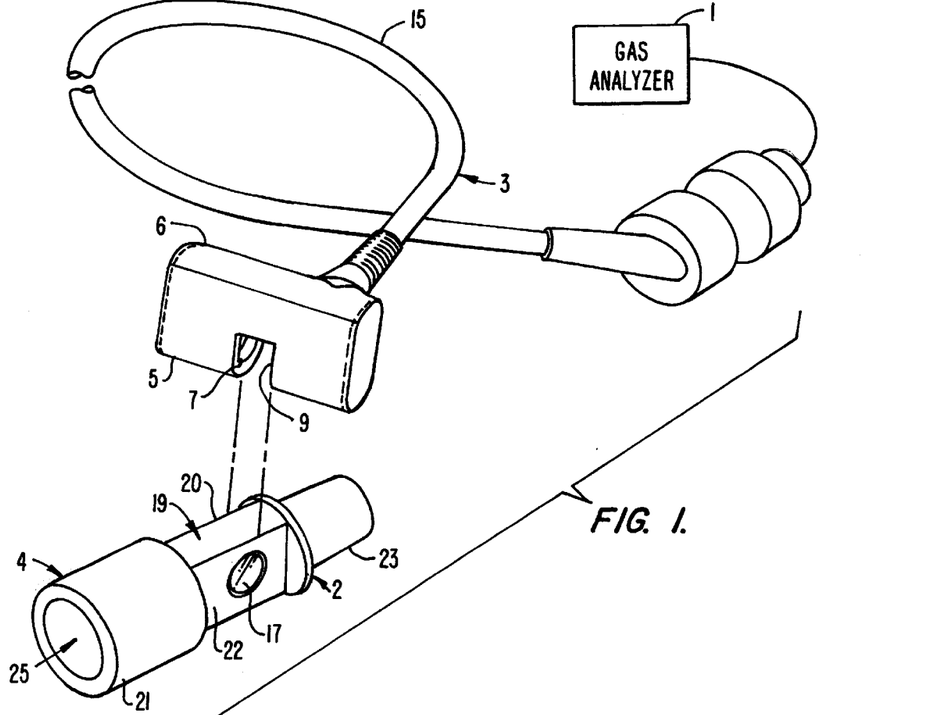
FIG. 1 is a perspective view of one embodiment of an airway adapter for use with a gas sensor and analyzer in accordance with the present invention.
Figure 2:
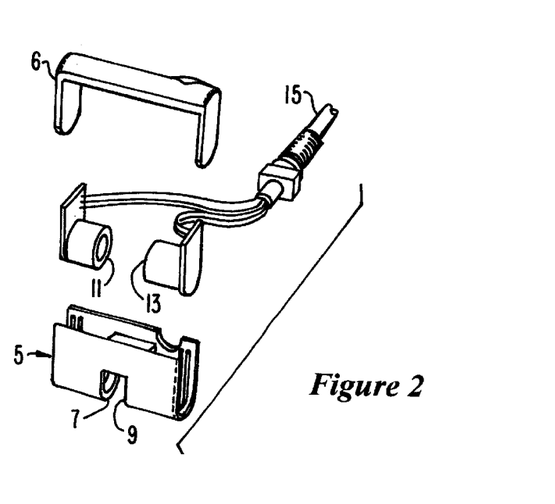
FIG. 2 is an exploded view of the gas sensor shown in FIG. 1.

The airway adapter 4 is configured to fit into the housing 5 of a gas sensor 3. One embodiment of a gas sensor 3 that may be used with the airway adapter 4 of the present invention is shown in FIGS. 1 and 2. Portions 7,9 of the gas sensor housing 5 extend down over a center section 19 of the cuvette or conduit 2 so as to accurately locate an infrared photo-emitter 11 and photo-detector 13 over windows 17 so that the photo-emitter and photo-detector are at a predetermined distance from each other. Housing member 6 is assembled with the housing 5 to enclose the photo-emitter 11 and photo-detector 13. An example of a commercially available gas sensor is Model N-6000 available from Nellcor, Inc., Pleasanton, Calif., 94588, the assignee of the present invention.

The photo-emitter 11 is preferably an infrared light source, such as the incandescent broad band lamp, Model OL-3070, manufactured by Oshino Lamps (5 volt, 1.6 amp, 2-1, ⅛ in. bulb). The photo-detector 13 contains an infrared detector and amplifier electronics. Signal connections are made via a cable 15 to gas analyzer 1.

The center section 19 of airway adapter 4 comprises a truncated cylinder with generally parallel sides 20,22. The airway adapter 4 also has two cylindrical end sections 21,23 with a sampling passage 25 extending from end-to-end through the adapter 4. The end sections 21,23 are axially aligned with center section 19. The central section 19 of the cuvette 2 provides a seat for the gas sensor 3.

FIGS. 3–7 show another embodiment of the airway adapter 4 in accordance with the present invention. The cylindrical end sections 21,23 are sufficiently tapered so as to form standard conical fittings for attachment to the tubing used to connect a patient to a mechanical ventilator or anesthesia breathing circuit. U-shaped flange 8 can be provided in some embodiments to help locate and maintain gas sensor 3 in the proper location on airway adapter 4. Protrusion 12 can also be provided to engage a detent on the gas sensor to help maintain the location of the gas sensor. Adapter 4 is preferably made from polypropylene, polyethylene, polysulfone or a comparable polymer.

Figure 3:
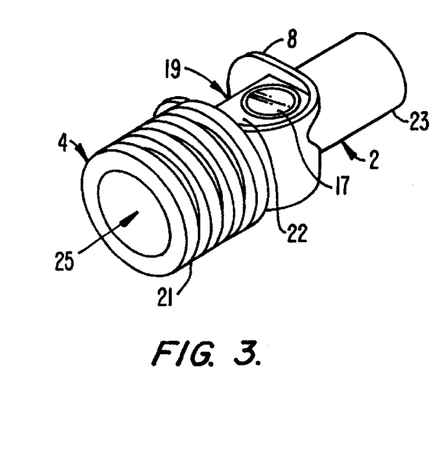
FIG. 3 is a perspective view of another embodiment of the airway adapter of the present invention shown rotated 90E counter-clockwise such that the right side of the airway adapter is facing upward.
Figure 3A:
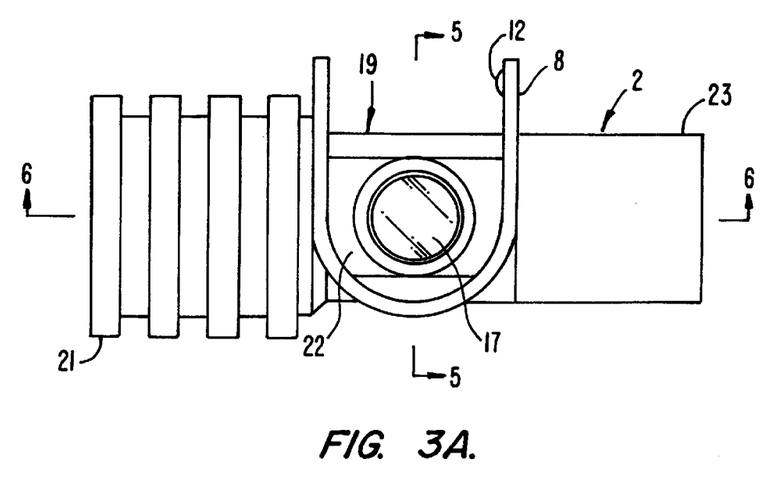
FIG. 3A is a right side view of the airway adapter shown in FIG. 3 rotated to its normal orientation.
Figure 4:
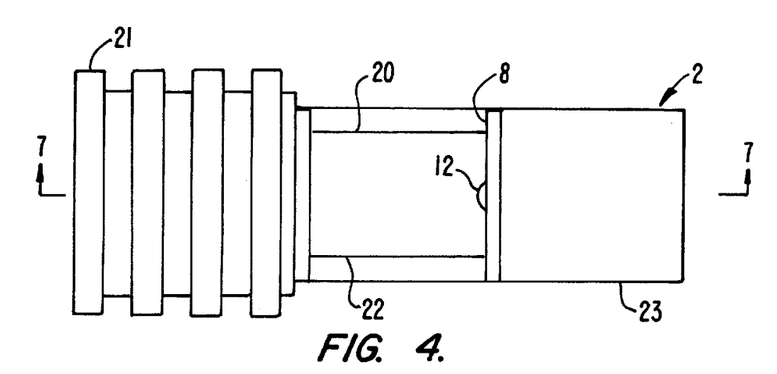
FIG. 4 is a top plan view of the airway adapter shown in FIG. 3A.
Figure 5:
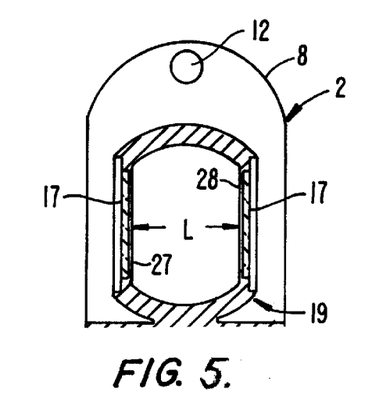
FIG. 5 is a cross-sectional view of the airway adapter in FIG. 3A taken along line 5—5.
Figure 6:
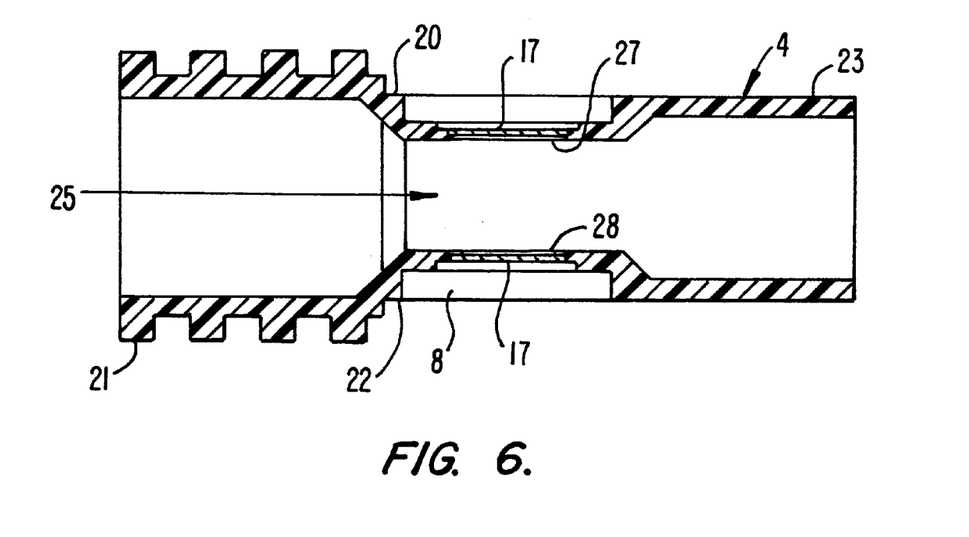
FIG. 6 is a cross-sectional view of the airway adapter in FIG. 3A taken along line 6—6.
Figure 7:
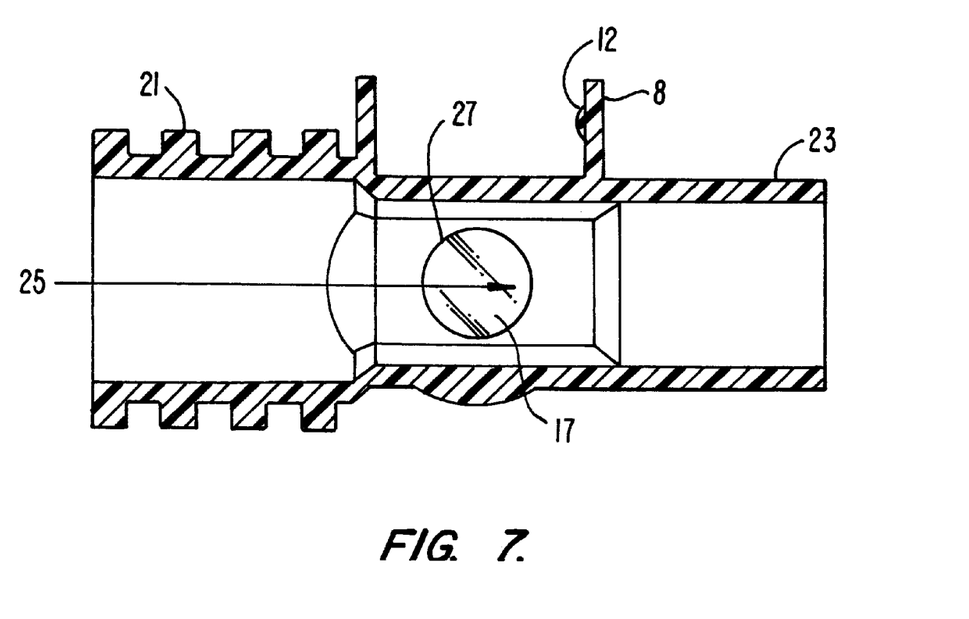
FIG. 7 is a cross-sectional view of the airway adapter in FIG. 4 taken along line 7—7.
Figure 8:
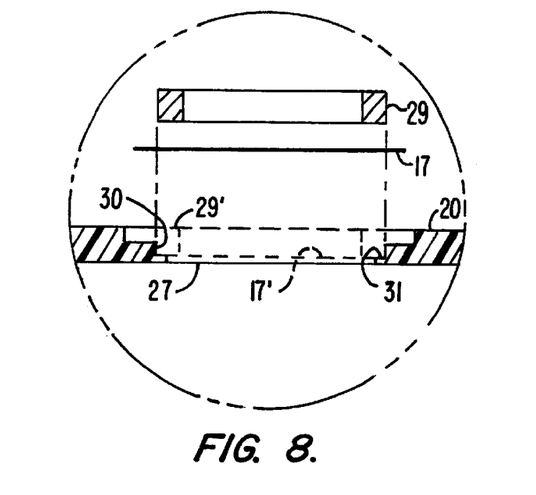
FIG. 8 is an enlarged view of one embodiment of the windows in accordance with the present invention.
Figure 9:
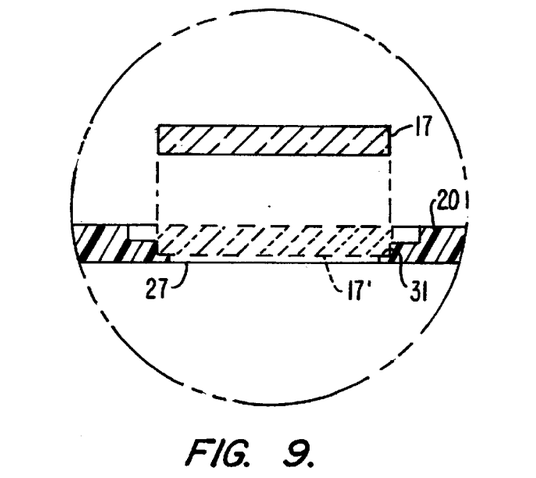
FIG. 9 is an enlarged view of another embodiment of the windows in accordance with the present invention.
Figure 10:
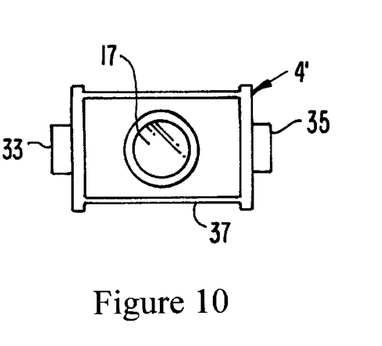
FIG. 10 is a side view of another embodiment of the airway adapter of the present invention.
Figure 11:
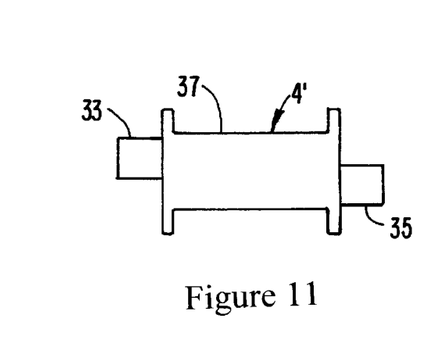
FIG. 11 is a top view of the airway adapter of FIG. 10.

As is best shown in FIGS. 3A and 5, openings or ports 27,28 are formed in the generally parallel sides 20,22 in the center section 19 of the cuvette 2. The openings or ports 27,28 are aligned and spaced in a predetermined widthwise configuration. FIG. 5 shows a cross-sectional view taken along line 5—5 in FIG. 3A of the airway adapter 4. The openings 27,28 define a predetermined path length distance identified by reference character L from each other. The optical path L extends from the infrared photo-emitter 11 in gas sensor 3 transversely across the cuvette or conduit 2 and the gas(es) flowing therethrough to the photo-detector 13. The airway adapter 4 is designed such that it conforms to the housing 5 of the gas sensor 3 so that a precision optical path length may be maintained even when less expensive materials such as plastic are used for forming the airway adapter.

The openings or ports 27,28 are sealed by windows 17 to keep the gas(es) flowing through the conduit 2 from escaping through openings 27,28 and to keep foreign material from entering the sampling passage 25 of the conduit 2. Perhaps even more importantly, these windows help to define the length of the optical path L for the radiation traversing the conduit 2. This is important because the radiation is attenuated to an extent proportional to the number of molecules of the designated constituent gas between the windows 17 and in that volume circumscribed by the windows. Consequently, even small volume variations can significantly affect the accuracy of a signal ultimately produced indicating the concentration of a designated constituent gas.

It is important to note that in another embodiment, the infrared photo-emitter 11 and photo-detector 13 can be located on the same side of cuvette or conduit 2 with a mirror on the other side of conduit 2 to reflect the radiation emitted from the photo-emitter back to the photo-detector.

As pointed out above, gas sensor 3 can be employed to measure the concentration of a designated gas(es) flowing through the sampling passage 25 in the airway adapter 4. As the monitoring of the gas(es) proceeds, and with the airway adapter 4 at ambient temperature, moisture (principally water vapor) can condense and collect on all surfaces including the windows 17 of the airway adapter 4. The condensation or fog is created when warm, moist gas(es) inside the respiratory circuit come(s) in contact with the cooler windows 17 of the airway adapter 4. The result may be a degradation in performance and loss of accuracy. The resulting condensation or fog absorbs some unknown portion of the infrared energy at the wavelengths used to measure carbon dioxide, anesthetic agents and other gas(es).

This problem is solved simply and elegantly in accordance with the present invention by using windows having surfaces that interact in a desired way with the moisture or water that condenses from the patient's breath so as to reduce the impact of the moisture on the monitoring of the constituent gases by the gas sensor 3. The window surface itself or a coating on the window having characteristics described herein, can be used in accordance with the present invention.

In one embodiment, the window surface or coating is sufficiently hydrophilic so as to wick away the condensation and form a water or moisture layer over the surface of the windows 17, which layer is sufficiently thin and uniform to enable accurate measurements to be conducted therethrough. The attenuation caused by the uniform thin layer of moisture is reduced to an acceptable level in the desired wavelengths. The attenuation resulting from a particular surface or coating is thereby uniform and consistent allowing compensation to be made and accuracy of measurement maintained. The hydrophilic surface or coating preferably should have 50% or less optical attenuation in the desired wavelengths. Generally speaking, the desired wavelengths are at or above 3 microns for detecting carbon dioxide. Depending on the agent, element, or compound to be detected, the desired wavelength may be anywhere between ultraviolet and infrared (i.e., 300 nm to 20,000 nm).

Figure 12:
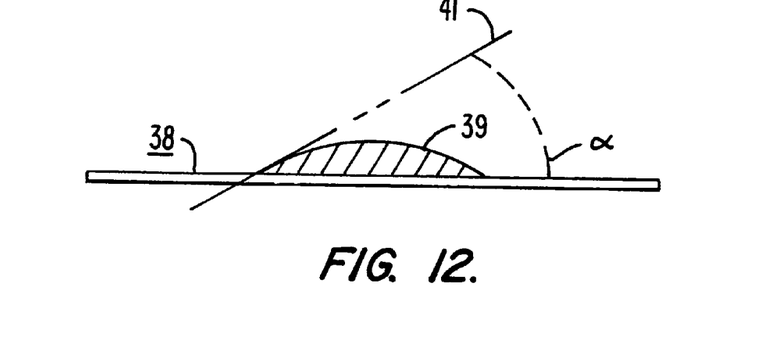
FIG. 12 is a schematic of a sessile drop contact angle for a hydrophilic surface.
Figure 13:
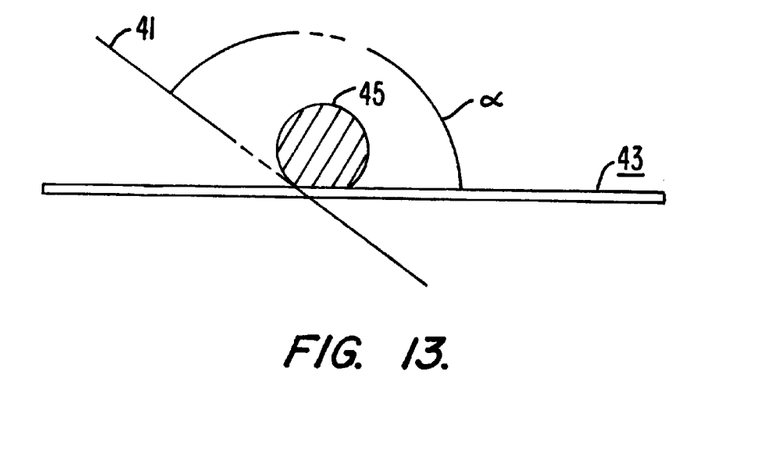
FIG. 13 is a schematic of a sessile drop contact angle for a hydrophobic surface.
Figure 14:
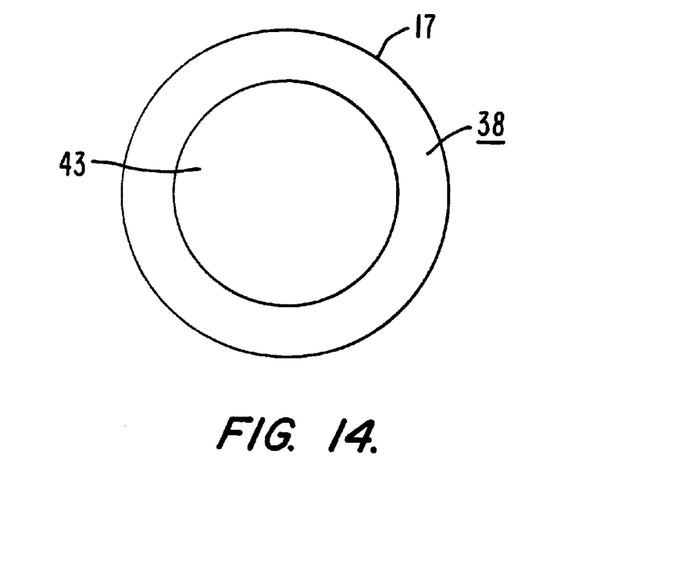
FIG. 14 is one embodiment of the windows in accordance with the present invention comprising a combination hydrophilic and hydrophobic surface.

A common measurement of the relative hydrophilicity of surfaces is the sessile drop contact angle " (FIG. 12), which is defined as that angle formed in the interior of the drop between surface 38 on which drop 39 rests and line 41 tangential to the drop at its point of contact with the surface. A surface is said to become more hydrophilic if the contact angle of the sessile drop is reduced. However, for substantial wicking action to occur, it is necessary that the work of adhesion between the polymer surface and liquid water be equal to or less than the work of cohesion of the liquid water itself. Under this condition, the liquid water can spread indefinitely over the surface, since energetically the system is indifferent to whether the water is in contact with the polymer or with itself. Contact angle " is readily measured by placing a drop of pure water (approximately 0.05 ml) on a clean and level surface. The drop is then imaged from the side with an optical microscope C or an image of the drop is projected onto a screen C and the contact angle is measured geometrically. The contact angle can also be measured using the Wilhelmi Plate Method of immersing a plate with a known surface area into a liquid with a known surface tension and measuring the force required to remove the plate.

Uncoated plastics such as polycarbonate, polyethylene, polypropylene, and polyester have contact angles of about 84E, 89E, 93E, and 90E respectively. In general, some polymers may be inherently hydrophilic to some degree and have contact angles greater than 50E. Sapphire has a contact angle of about 90E. If the contact angle is greater than about 50E, as may occur for example in polymers that are neither coated nor have any other type of hydrophilic surface modification, the surface is insufficiently hydrophilic for this embodiment of the invention. Preferably the hydrophilic surface produces a sessile drop contact angle of about 50E or less, more preferably about 20E or less, and most preferably about 10E or less. The particularly preferred surface has a contact angle in the range of about 2.5E to about 5E for optimum performance.

Polymeric materials such as polyurethane coated polyester exhibit a high degree of hydrophilicity C sessile drop contact angle of about 19E C and can be used with the present invention. Other materials such as "VISTEX," a polyester terephthalate and aliphatic urethane interpolymer with polyvinyl pyrrolidone which is preferred, (available from Film Specialties, Inc., Whitehouse, N.J.), or polyacrylamide, polyvinylpyrrolidone, polyethylene glycol, hyaluronic acid, heparin, and polyacrylamide-heparin complexes can be used also. Compounds with carboxylic moiety and similar oxygen rich moieties, or polymers terminating with a 2-pyrrolidinone group (also called pyrrolidone), a 4(3H)-pyrimidone group, or a levulinic acid also exhibit a high degree of hydrophilicity.

If a surface coating is used, it can be applied to the surface of windows 17 as a film or liquid coating or with a photochemically coupling process, a copolymer formation process, a plasma polymerization process, vacuum deposition process or an ozonation technique.

In another embodiment of the present invention, the surface of the windows 17 or the coating can be hydrophobic. The hydrophobicity causes the condensation to form droplets. The droplets form interstices between the droplets that are substantially clear and dry such that sufficient energy at the desired wavelengths traverses the airway adapter through windows 17 for accurate measurements. The hydrophobic surface or coating preferably should have 50% or less optical attenuation in the desired wavelengths. Generally speaking, the desired wavelengths are at or above 3 microns for detecting carbon dioxide. Depending on the agent, element, or compound to be detected, the desired wavelength may be anywhere between ultraviolet and infrared (i.e., 300 nm to 20,000 nm).

As with the relative hydrophilicity discussed previously, a common measurement of the relative hydrophobicity of surfaces is the sessile drop contact angle " (FIG. 13), which is defined as that angle formed in the interior of the drop between surface 43 on which drop 45 rests and line 41 tangent to the drop at its point of contact with the surface. A surface is said to become more hydrophobic if the contact angle of the sessile drop is increased. For substantial condensing of the droplets to occur, the work of adhesion between the polymer surface and liquid water must be greater than the work of cohesion of the liquid water itself. Under this condition, liquid water cannot spread indefinitely over such a surface, it must form compact drops since energetically the system is sensitive to whether the water is in contact with the surface or with itself. Therefore, the liquid water can form substantial droplets spaced across the surface. Contact angle " is readily measured as discussed previously.

Some materials may be inherently hydrophobic to some degree. If the contact angle is 93E or less, as occurs for example on materials that are neither coated nor have any other type of hydrophobic surface modification such as polycarbonate, polyethylene, polypropylene and polyester mentioned above, the surface is insufficiently hydrophobic for this embodiment of the invention. Preferably, the hydrophobic surface produces a sessile drop contact angle of 94E or greater, more preferably about 100E or greater, and most preferably about 120E or greater. A particularly preferred surface has a contact angle of about 160E or greater for optimum performance.

Materials that exhibit strong hydrophobicity and can be used in accordance with the present invention include polymers such as tetrafluoroethylene fluorocarbon polymers C sessile drop contact angle of about 105E C and fluorinated ethylene-propylene resins sold under the trade names "TEFLON AF" and "TEFLON PFA" (available from E. I. Du Pont de Nemours, Co., Wilmington, Del.) and silicone resin-colloidal silica complexes such as the one sold under the trade name "SILVUE XF-094" (available from SDC Coatings, Inc., Anaheim, Calif.).

FIG. 8 shows a close-up view of one embodiment of the windows 17 of the present invention in which the window 17 is a polymeric material, preferably a film, which inherently has surface characteristics as described herein or has its surface coated with a material having surface characteristics described herein. Such materials are preferably used since they are inexpensive, transparent to infrared energy and relatively rigid, yet are not susceptible to moisture condensation. An annular seat 31 is provided in each port 27,28 for receiving the windows 17. In this embodiment, the polymeric window 17 is pressed into the annular seat 31 and held in place by friction press fit with the compression ring 29.

In one embodiment, window 17 is placed over each port 27,28. Then the compression ring is used to stretch window 17 taut as the compression ring is pressed into seat 31. The window 17 has a diameter slightly larger than the diameter of annular seat 31 and the diameter of the compression ring. In this way, window 17 is secured to airway adapter 4 along receiving surface 30. With the use of the compression ring, the window goes from a relaxed state to a stretched state in order to hold the optical path length L constant. It is important that the windows do not have any wrinkles, waves, deformations, etc. because even small variations in the optical path can significantly affect the accuracy of an ultimately produced, concentration indicative signal. The seated position of the window is shown as 17N and of the compression ring as 29N. Compression ring 29 can be plastic or metallic. In another embodiment, the plastic or i metallic compression ring can be used in conjunction with a heater to heat the window and rid the window of moisture whether the window is hydrophobic, hydrophilic or neither. Plastic can be used to achieve the desired amount of heat conduction to accomplish the drying function because the ring is small and the amount of heat to be supplied is small.

In other embodiments, the polymeric window 17 can be held in place by heat pressing the window periphery around the annular seat, by heat staking or by adhering the window to the adapter body by some other acceptable adhering technique such as ultrasonic bonding or by using a suitable adhesive.

In another embodiment, sapphire windows with either a hydrophobic or hydrophilic surface film, coating or treatment as described herein can be used with the present invention because they absorb very little infrared radiation in the desired wavelengths. FIG. 9 shows a close-up view of such an embodiment. In a preferred embodiment, the sapphire window 17 is pressed into the annular seat 31 and held in place by a friction press fit or with a suitable adhesive. The seated position of the window is shown as 17N. The sapphire window can also be held in place by heat pressing the window periphery around the annular seat, by heat staking, or by ultrasonic bonding.

FIGS. 10 and 11 show another embodiment of the airway adapter of the present invention. The airway adapter 4N is used for patients who are not intubated with an endotracheal tube and must be monitored with a nasal cannula. The nasal cannula is a flexible tube which is placed slightly within the nostrils. A pump continuously withdraws gas from the nasal cannula through the airway adapter 4N. The airway adapter 4N is fitted with the same windows 17 in the same optical arrangement as the airway adapters previously described. FIG. 11 shows that the inlet 33 and outlet 35 are placed off center in order to ensure that the constituent gas(es) passing through the sampling chamber 37 are well mixed for accurate analysis.

As will be appreciated by one of ordinary skill in the art, the coating or surface of the windows 17 can also be a combination of hydrophilic and hydrophobic properties. FIG. 14 illustrates one embodiment of window 17 with a hydrophobic surface 43 surrounded by a hydrophilic surface 38. In this way, the hydrophilic portion can wick the condensation away from the hydrophobic portion thus minimizing the amount of water collected on the hydrophobic area. Alternatively, the hydrophobic portion can urge the condensation to the hydrophilic portion. Various patterns of alternating hydrophobic and hydrophilic areas can be used, such as strips, dots, checks, concentric rings, etc., to control the condensation on the surface so that the desired accuracy of measurements can be achieved. In other embodiments of the invention, the entire or a portion of the inside and/or outside of the airway adapter can be hydrophilic, hydrophobic, or a combination thereof.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An airway adapter for use with a respiratory gas analyzer comprising:

a tubular portion having a window positioned whereby respiratory gases passing through the adapter flow past said window and being adapted to receive an emitter and a receiver for measuring through the window energy absorbance of a constituent gas in the respiratory gases;

wherein said window comprises at least one surface producing a sessile drop contact angle of 50E or less which interacts with moisture condensed thereon from the respiratory gases so as to reduce the interference of such condensation with the measurement of the constituent gas by the gas analyzer.

2. The airway adapter of claim 1 wherein said surface produces a sessile drop contact angle of 20E or less.

3. The airway adapter of claim 1 wherein said surface produces a sessile drop contact angle of 10E or less.

4. The airway adapter of claim 1 wherein said surface comprises a polymeric material.

5. The airway adapter of claim 1 wherein said surface provides 50% or less optical attenuation at a wavelength at or above 3 microns.

6. The airway adapter of claim 1 wherein said surface is sufficiently hydrophilic to form the condensation into a layer sufficiently thin and uniform to permit measurement of the constituent gas through said layer.

7. The airway adapter of claim 1 wherein said surface is a polyurethane coating, a polyacrylamide coating, a polyvinylpyrrolidone coating, a polyethylene glycol coating, a hyaluronic acid coating, a heparin coating, or a polyacrylamide-heparin complex coating.

8. The airway adapter of claim 7 wherein said surface coating is applied to said window with a photochemically coupling process, a copolymer formation process, a plasma polymerization process, or an ozonation technique.

9. The airway adapter of claim 1 wherein said surface is a compound with carboxylic moiety and similar oxygen rich moieties.

10. The airway adapter of claim 9 wherein said surface is a polymer terminating with the 2-pyrrolidinone group (also called pyrrolidone), a polymer terminating with the 4(3H)-pyrimidone group, or a polymer terminating with the levulinic acid moiety.

11. The airway adapter of claim 1 wherein a portion of said at least one surface produces a sessile drop contact angle of 94E or greater, wherein said portion urges the condensation to another portion which produces a sessile drop contact angle of 50E or less.

12. The airway adapter of claim 1 wherein said airway adapter has an area which produces a sessile drop contact angle of 94E or greater to provide control of the physical form of the condensation.

13. The airway adapter of claim 1 comprising:

a pair of opposing windows in said tubular portion providing a predetermined optical path length for measuring the energy absorbance of the constituent gas.

14. An airway adapter for use with a respiratory gas analyzer comprising:

a tubular portion having a window positioned whereby respiratory gases passing through the adapter flow past said window and being adapted to receive an emitter and a receiver for measuring through the window energy absorbance of a constituent gas in the respiratory gases;

wherein said window comprises at least one surface producing a sessile drop contact angle of 94E or greater which interacts with moisture condensed thereon from the respiratory gases so as to reduce the interference of such condensation with the measurement of a constituent gas by the gas analyzer.

15. The airway adapter of claim 14 wherein said surface produces a sessile drop contact angle of 100E or greater.

16. The airway adapter of claim 14 wherein said surface produces a sessile drop contact angle of 120E or greater.

17. The airway adapter of claim 14 wherein said surface is sufficiently hydrophobic to form the condensation into droplets sufficiently defined to form interstices therebetween that permit measurement of a constituent gas through said interstices.

18. The airway adapter of claim 14 wherein said surface is tetrafluoroethylene fluorocarbon polymer or fluorinated ethylene-propylene resin.

19. The airway adapter of claim 14 wherein said surface is a silicone resin- colloidal silica complex coating.

20. The airway adapter of claim 14 wherein a portion of said at least one surface produces a sessile drop contact angle of 50E or less, wherein said portion wicks the condensation from the portion producing a sessile drop contact angle of 94E or greater.

21. The airway adapter of claim 14 wherein said airway adapter has an area which produces a sessile drop contact angle of 50E or less to provide control of the physical form of the condensation.

22. The airway adapter of claim 14 comprising:

a pair of opposing windows in said tubular portion providing a predetermined optical path length for measuring the energy absorbance of the constituent gas.

23. A method for measuring the energy absorbance of a constituent gas in respiratory gases comprising:

providing a respiratory gas analyzer having an emitter and a receiver;

providing an airway adapter having a tubular portion having opposing windows positioned whereby the respiratory gases pass through the adapter and flow between said opposing windows, said airway adapter being adapted to receive the emitter and receiver for measuring through the windows the energy absorbance of the constituent gas;

wherein said windows comprise at least one surface producing a sessile drop contact angle of 50E or less which interacts with moisture condensed thereon from the respiratory gases so as to reduce the interference of such condensation with the measurement of the constituent gas by the gas analyzer; and measuring the energy absorbance of the constituent gas in the respiratory gases with the respiratory gas analyzer.

24. A method for measuring the energy absorbance of a constituent gas in respiratory gases comprising:

providing a respiratory gas analyzer having an emitter and a receiver;

providing an airway adapter having a tubular portion having opposing windows positioned whereby the respiratory gases pass through the adapter and flow between said opposing windows, said airway adapter being adapted to receive the emitter and receiver for measuring through the windows the energy absorbance of the constituent gas;

wherein said windows comprise at least one surface producing a sessile drop contact angle of 94E or greater which interacts with moisture condensed thereon from the respiratory gases so as to reduce the interference of such condensation with the measurement of the constituent gas by the gas analyzer; and measuring the energy absorbance of the constituent gas in the respiratory gases with the respiratory gas analyzer.

* * * * *